US00PP34577P2

(12) United States Plant Patent
Rotteveel

(10) Patent No.: US PP34,577 P2
(45) Date of Patent: Sep. 13, 2022

(54) ***GERANIUM* PLANT NAMED 'INTENSE'**

(50) Latin Name: ***Geranium* x *cantabrigiense***
Varietal Denomination: 'INTENSE'

(71) Applicant: Gebroeders Rotteveel vof, Noordwijkerhout (NL)

(72) Inventor: Roy Rotteveel, Noordwijkerhout (NL)

(73) Assignee: Gebroeders Rotteveel VOF

( * ) Notice: Subject to any disclaimer, the term of this patent is extended or adjusted under 35 U.S.C. 154(b) by 0 days.

(21) Appl. No.: 17/375,828

(22) Filed: Jul. 14, 2021

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/425
See application file for complete search history.

(56) References Cited

PUBLICATIONS

CPVO Application Consultation, CPVO register, application No. 20210560, filed Feb. 24, 2021 for a *Geranium* ×cantabrigiense plant named, 'INTENSE', downloaded from https://online.plantvarieties.eu/publicConsultationDetails?registerId=20210560&denomination=intense.*

UPOV PLUTO database, variety of *Geranium* plant named, 'INTENSE', QZ PBR 20210560, filed Feb. 24, 2021, downloaded from www.upov.int.*

Trademark Electronic Search System (TESS), Intense, serial No. 77108439, filed Feb. 15, 2007, downloaded from https://tmsearch.uspto.gov/bin/showfield?=doc&state=4805:126qd3.2.4.*

* cited by examiner

*Primary Examiner* — Anne Marie Grunberg
(74) *Attorney, Agent, or Firm* — Cassandra Bright

(57) ABSTRACT

A new and distinct cultivar of *Geranium* plant named 'INTENSE' is disclosed, characterized by bright pink flowers, and green foliage with red coloration in Autumn. Plants are floriferous and have a spreading, mounding growth habit. The new variety is a *Geranium*, typically produced as an outdoor ornamental plant.

5 Drawing Sheets

Latin name of the genus and species: *Geranium* x *cantabrigiense.*

Variety denomination: 'INTENSE'.

BACKGROUND OF THE INVENTION

The new cultivar was selected as a single seedling plant discovered in a field of various unpatented *Geranium* x *cantabrigiense* varieties. The parent varieties cannot be identified.

The new variety was found and selected by the inventor in 2015 in a nursery field in Noordwijk, the Netherlands. After identifying the new variety as a potentially interesting selection, the inventor continued confidential trial growing of 'INTENSE' to assess the stability of characteristics unique to this variety.

Asexual reproduction of the new cultivar 'INTENSE' was first performed during 2015 at a nursery in Noordwijk, the Netherlands by vegetative cuttings. Through subsequent propagation multiple additional generations have been reproduced, having shown that the unique features of this cultivar are stable and reproduced true to type.

SUMMARY OF THE INVENTION

The cultivar 'INTENSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'INTENSE'. These characteristics in combination distinguish 'INTENSE' as a new and distinct *Geranium* cultivar:

1. Bright pink flowers.
2. Spreading, mounding habit.
3. Green leaves with red coloration in Autumn.
4. Very floriferous plants.

PARENT COMPARISON

Parent varieties are unknown.

COMMERCIAL COMPARISON

*Geranium* 'INTENSE' can be compared to compared to the commercial variety *Geranium* 'Karmina', unpatented. Plants of 'INTENSE' are similar to plants of 'Karmina' in most horticultural characteristics, however, plants of 'INTENSE' differ in the following:

1. Flowers of 'INTENSE' are a darker, brighter pink than flowers of 'Karmina'.

'INTENSE' can be compared to compared to the commercial variety *Geranium* 'Cambridge', unpatented. Plants of 'INTENSE' are similar to plants of 'Cambridge' in most horticultural characteristics, however, plants of however, plants of 'INTENSE' differ in the following:

1. Flowers of 'INTENSE' are darker, brighter pink than flowers of 'Cambridge'.

'INTENSE' can be compared to compared to the commercial variety *Geranium* 'ABPP', U.S. Plant Pat. No. 20,809. Plants of 'INTENSE' are similar to plants of 'ABPP', in most horticultural characteristics, however, plants of however, plants of 'INTENSE' differ in the following:

1. Flowers of 'INTENSE' are a darker, brighter pink than flowers of 'ABPP'.
2. Plants of 'INTENSE' are more compact than plants of 'ABPP'.

BRIEF DESCRIPTION OF THE PHOTOGRAPHS

The accompanying photograph in FIG. 1 illustrates in full color a typical plant of 'INTENSE' grown outdoors in Boskoop, the Netherlands. This plant is approximately 18 months old, grown in a 19 cm pot.

Figure 1:
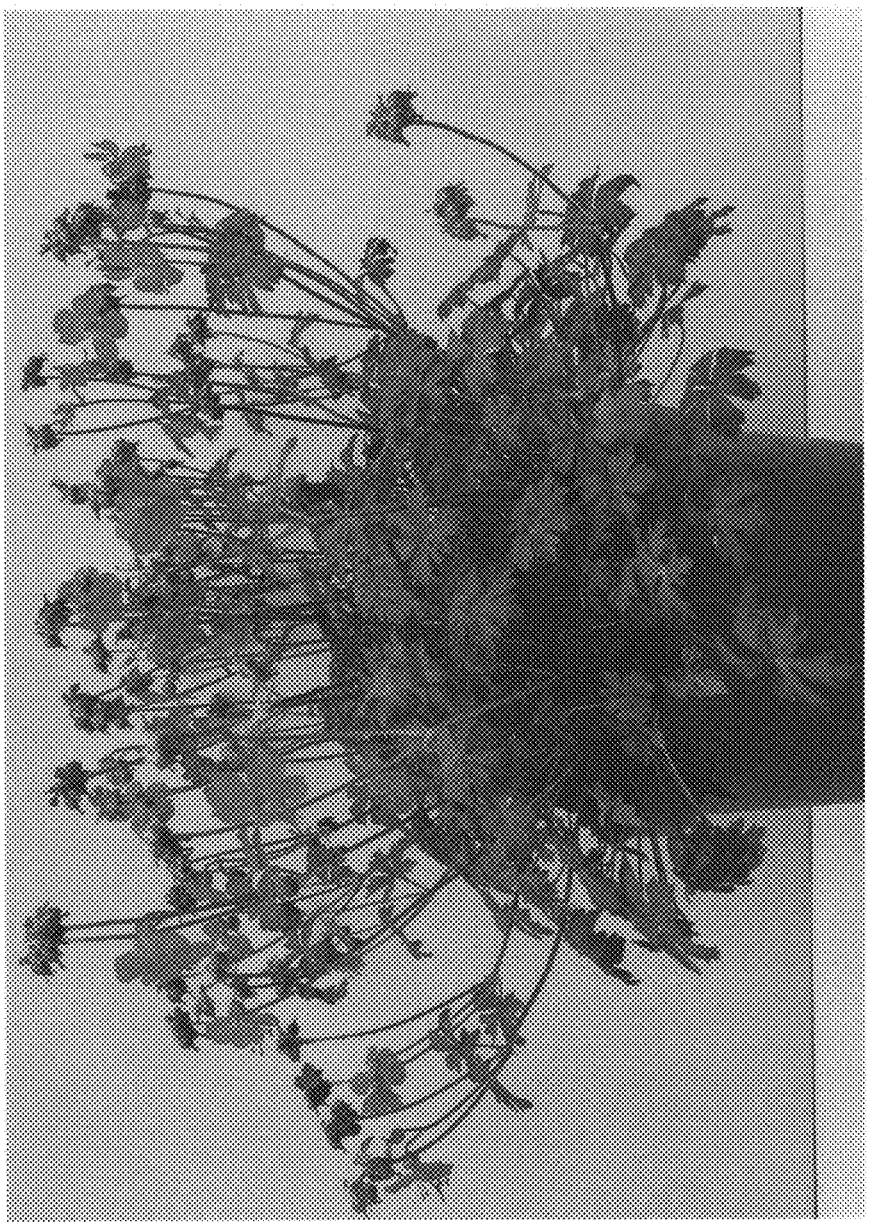
Figure 2:
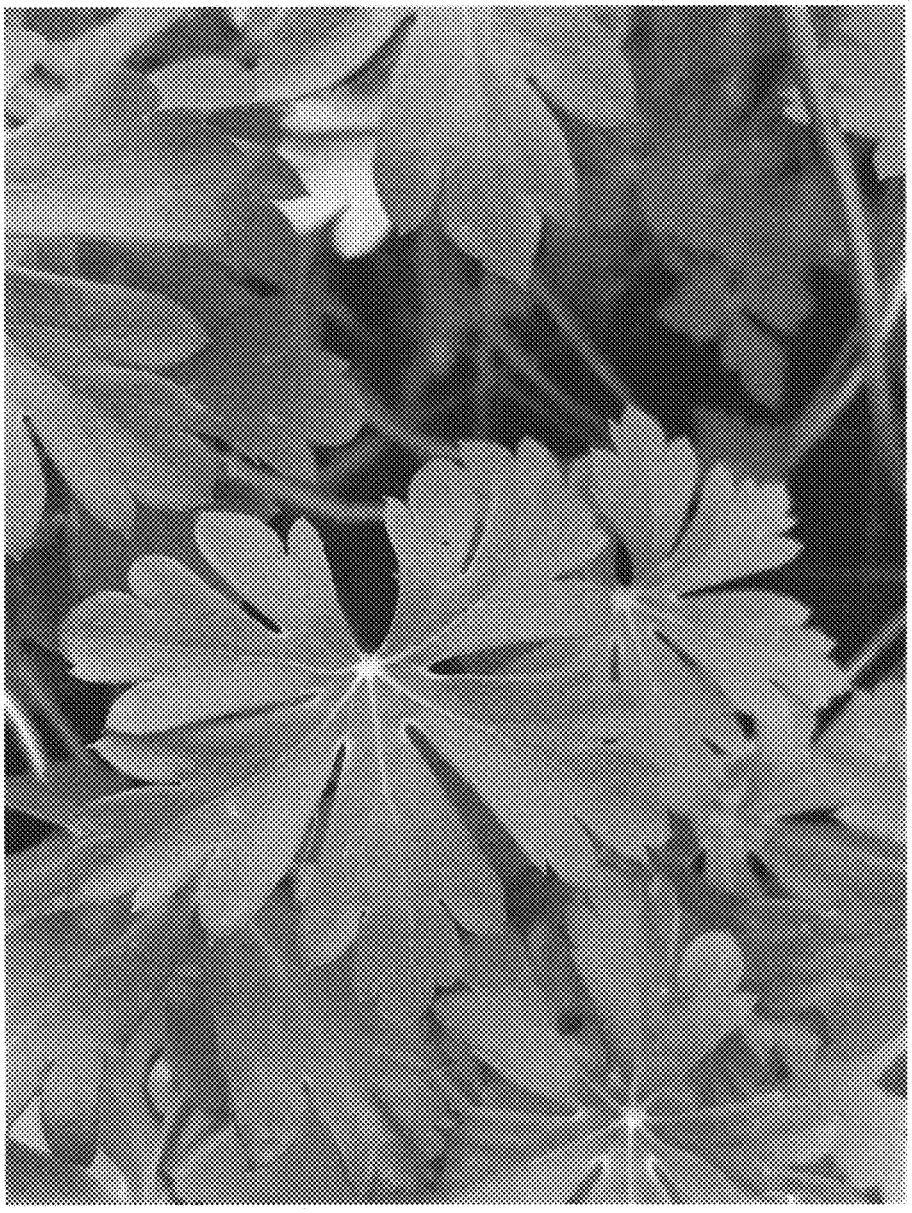
FIG. 2 illustrates in full color a close up of mature foliage of 'INTENSE'.
Figure 3:
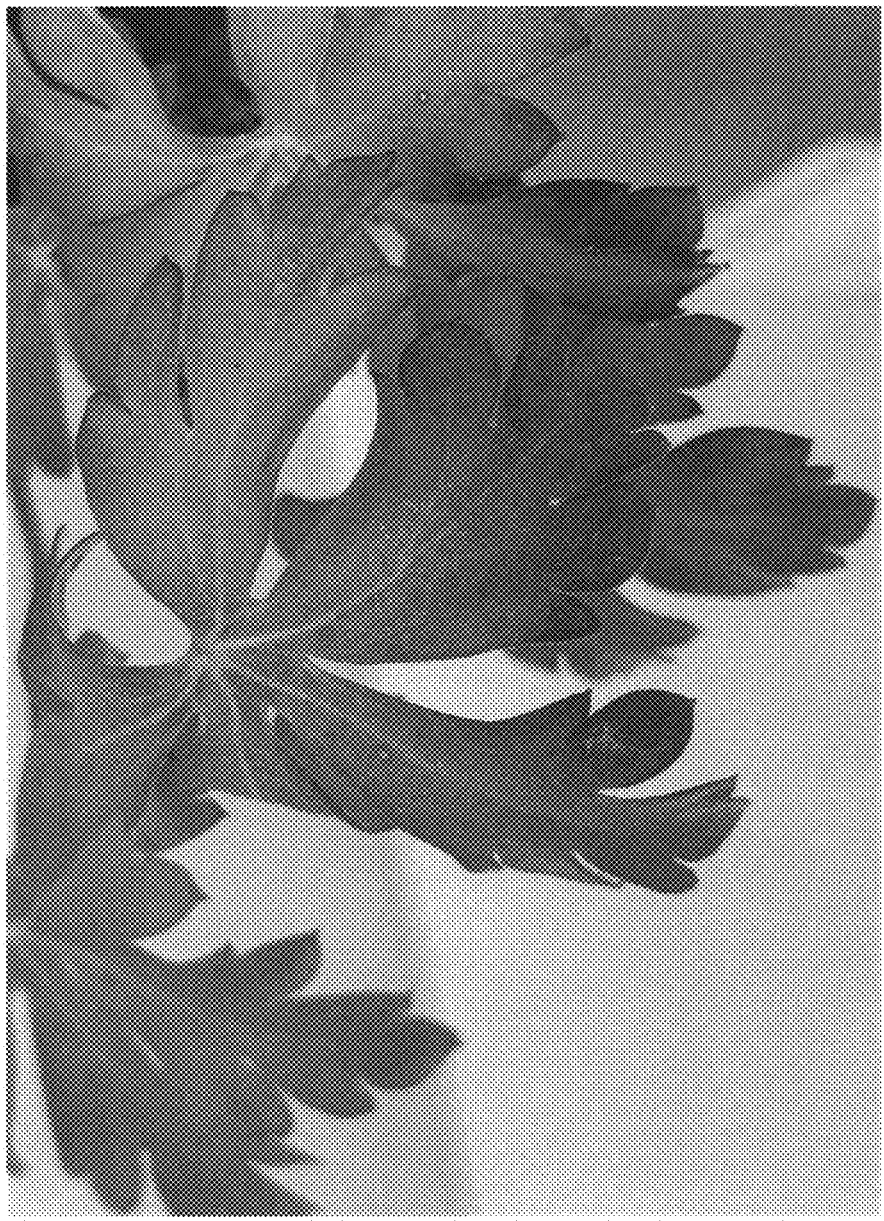
FIG. 3 illustrates a Fall foliage, with red bronzing.
Figure 4:
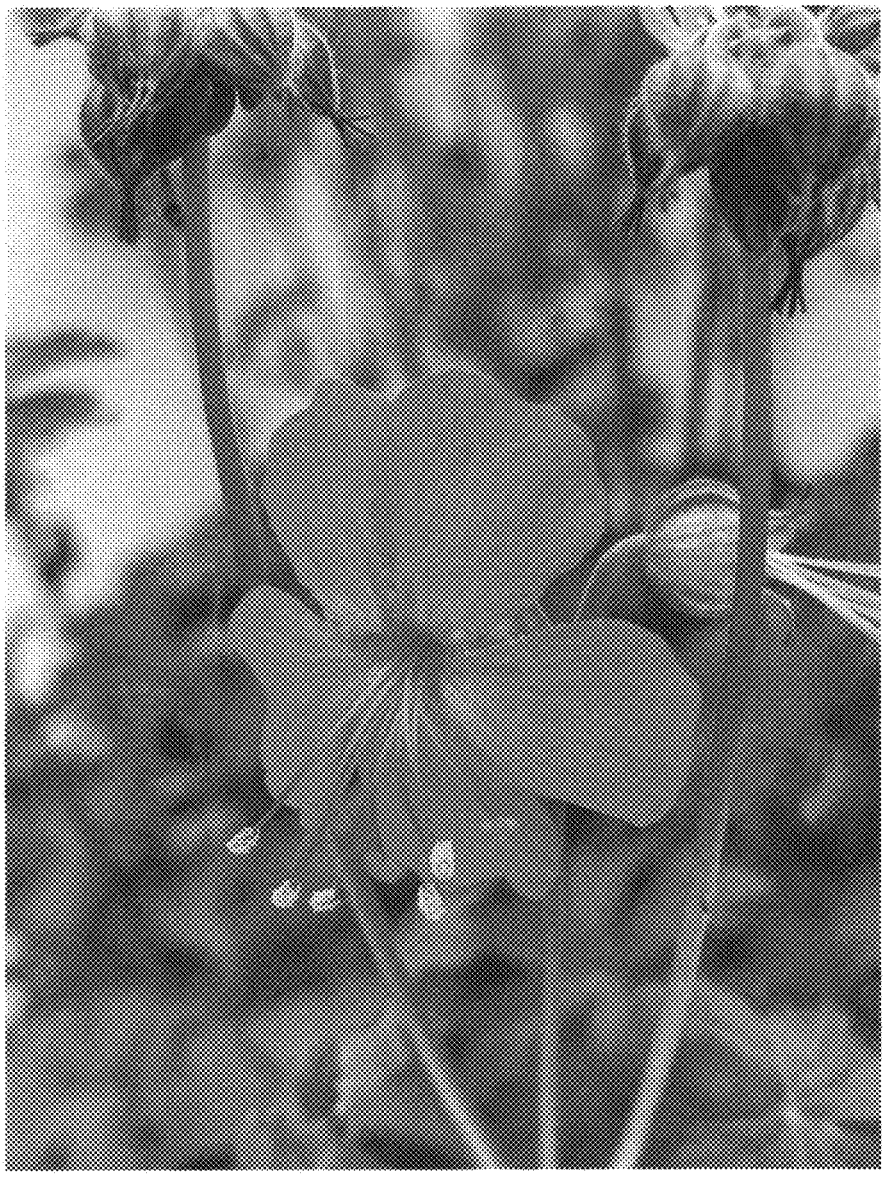
FIG. 4 illustrates a close-up view of a typical flower.
Figure 5:
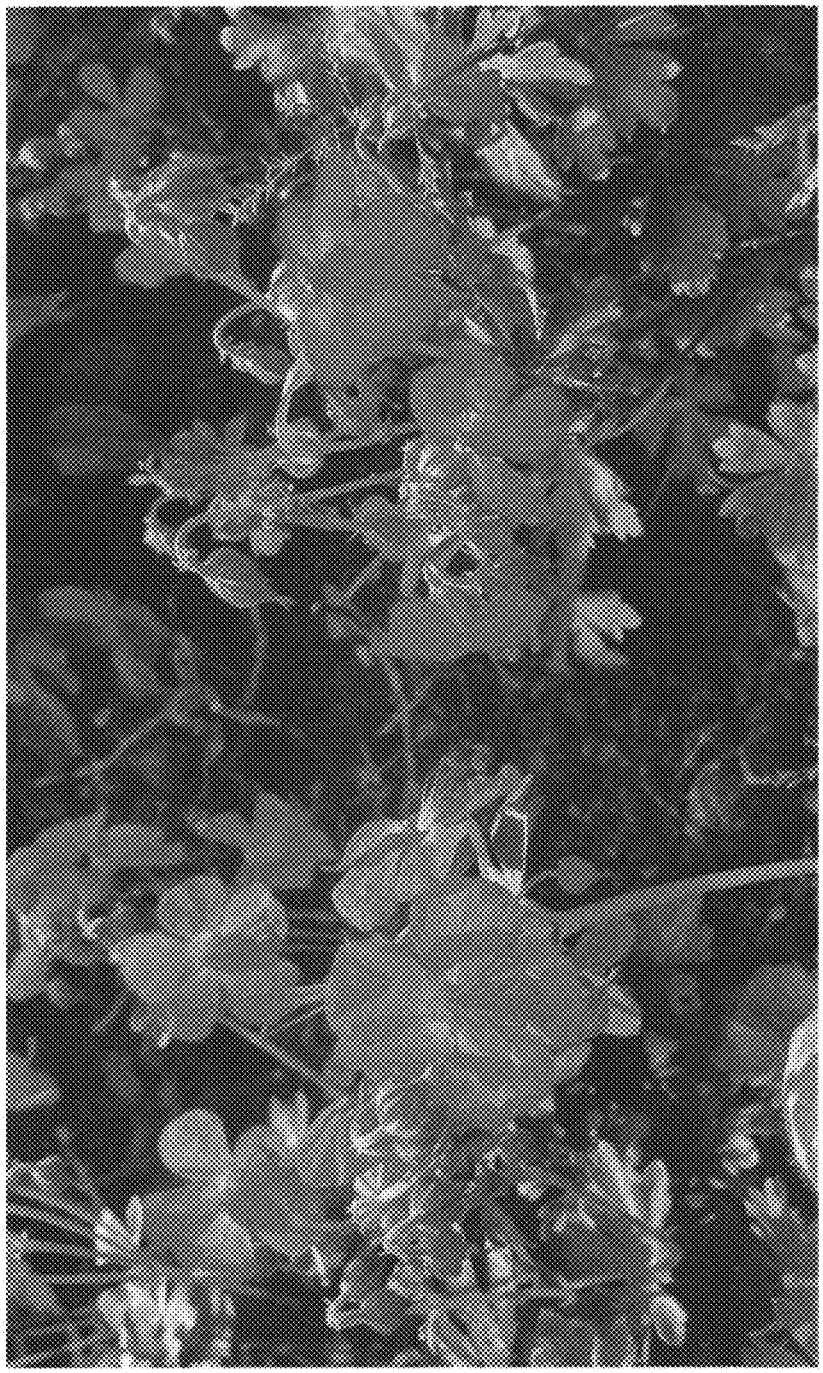
FIG. 5 illustrates a flowering of the new variety on the right of the figure and a flower of the comparator 'Crystal Rose' on the left of the figure.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'INTENSE' plants grown outdoors in Boskoop, the Netherlands. Temperatures ranged from −5° C. to 25° C. at night to 5° C. to 32° C. during the day. No artificial light, photoperiodic treatments were given to the plants. Measurements and numerical values represent averages of typical plant types.

Botanical classification: *Geranium* x *cantabrigiense* 'INTENSE'.

PROPAGATION

Typical method: Cuttings.

Root initiation: 2 to 3 weeks. 5 weeks from rooted cutting to a young plant.

PLANT

Plant type: Perennial.
Growth habit: Mounding, dense.
Height: 23 cm.
Plant spread: 47 cm.
Pot size of plant described: 19 cm.
Age of plant described: Approximately 18 months.
Growth rate: Vigorous.
Primary stem:
- *Branching*.—Basal.
- *Shape*.—Cylindrical.
- *Color*.—RHS Yellow-Green 145A.
- *Length*.—About 2 cm.
- *Width*.—3 mm.
- *Texture*.—Very slightly pubescent.
- *Fragrance*.—Light lemon scent.
- *Secondary stem*.—Length: Approximately 14 cm up to the peduncle. Width: 3 mm.

FOLIAGE

Leaf:
- *Shape*.—Palmate.
- *Average length* (*excluding petiole*).—Approximately 4.5 cm.
- *Average width*.—Approximately 5 cm.
- *Quantity per lateral branch*.—Approximately 28 per stem.
- *Apex*.—Acute.
- *Base*.—Auriculate.
- *Margin*.—Lobed and dentate.
- *Texture of top surface*.—Glabrous.
- *Texture of bottom surface*.—Slightly pubescent.
- *Color*.—Young foliage upper side: Near RHS Green 137C. Young foliage under side: Near RHS Green 137C. Mature foliage upper side: Near RHS Green 137A, some leaves very slightly margined with Greyed-Purple 185A. Mature foliage under side: Near RHS Green 137A, some leaves very slightly margined with Greyed-Purple 185A. Fall foliage upper side: Near RHS Green 137C flushed Greyed-Purple 187A. Fall foliage under side: Near RHS Green 137C flushed Greyed-Purple 187A.
- *Fragrance*.—Lemon scent.

Venation:
- *Type*.—Pinnipalmate.
- *Color*.—RHS Yellow-Green 145A.

Petiole:
- *Length*.—1.5 to 9 cm.
- *Width*.—Approximately 1 mm.
- *Color*.—Near RHS Yellow-Green 145A, fading Purple-Brown 187A towards the top.

INFLORESCENCE

Natural flowering season: Early May through July in the Netherlands.
Quantity of flowers: About 250 flowers and flower buds per plant.
Inflorescence type: Umbel.
Flower shape: Rotate.
Flowers persistent or self-cleaning: Self-cleaning.
Fragrance: None detected.
Flower size:
- *Diameter*.—Approximately 2.7 cm.

Petals:
- *Number per flower*.—5.
- *Margin*.—Entire.
- *Apex*.—Emarginate.
- *Length*.—Approximately 1 cm.
- *Width*.—Approximately 0.7 cm.
- *Shape*.—Obovate.
- *Base*.—Attenuate.
- *Texture*.—Glabrous.
- *Color*.—When opening: Upper Side: RHS Pink-Purple N74A. Under Side: RHS Pink-Purple N74A. Fully Opened: Upper Side: RHS Pink-Purple N74B. Under Side: RHS Pink-Purple N74B.

Bud:

*Shape*.—Ovoid.

*Length*.—6 cm.

*Diameter*.—5 cm.

*Surface*.—Pubescent.

*Color*.—RHS Green 146C, flushed Red 53C.

Sepals:

*Quantity*.—5 per flower.

*Margin*.—Entire.

*Fused or unfused*.—Unfused.

Calyx:

*Shape*.—Urceolate.

*Surface*.—Ribbed.

*Height*.—0.9 cm.

*Width*.—0.5 cm.

*Color*.—RHS Green 146C, with hints of Red 53C.

Peduncles:

*Length*.—7 to 9 cm.

*Diameter*.—1.5 mm.

*Color*.—RHS Yellow-Green 145A, with Purple-Brown 183A. Fully Yellow-Green 145A at base and top.

*Surface*.—Slightly pubescent.

Pedicle:

*Length*.—0.8 cm.

*Width*.—1 mm.

*Surface*.—Slightly pubescent.

*Color*.—RHS Yellow-Green 145A, with Red 53C.

REPRODUCTIVE ORGANS

Stamens:

*Number*.—10.

*Color*.—RHS Red-Purple N57A. Base near Purple-Pink N74D.

*Length*.—Approximately 1 cm.

Anthers:

*Length*.—Approximately 2 mm.

*Color*.—Near RHS Red 53C.

*Pollen*.—Scant.

*Pollen color*.—RHS Orange-Yellow 13B.

Pistil:

*Length*.—1.3 cm.

*Color*.—RHS Pink-Purple 71B.

Stigma:

*Length*.—1 mm.

*Shape*.—Diverges into 5 sections at apex.

*Color*.—RHS Pink-Purple 71B.

*Ovary height*.—2.5 mm.

*Ovary diameter*.—2.5 cm.

*Ovary color*.—RHS Yellow-Green 145A.

OTHER CHARACTERISTICS

Disease resistance: Neither resistance nor susceptibility to the normal diseases and pests of *Geranium* has been observed.

Temperature tolerance: USDA Zones 3 through 8.

Drought tolerance: None observed.

Fruit/seed production: Not observed to date.

What is claimed is:

1. A new and distinct cultivar of *Geranium* plant named 'INTENSE' as herein illustrated and described.

* * * * *